United States Patent [19]

Hadary

[11] Patent Number: 4,672,986
[45] Date of Patent: Jun. 16, 1987

[54] TOOTHPICK HOLDER

[76] Inventor: Joseph Hadary, 5405 Linden Ct., Bethesda, Md. 20814

[21] Appl. No.: 819,112

[22] Filed: Jan. 15, 1986

[51] Int. Cl.⁴ ............................................. A61C 15/00
[52] U.S. Cl. ........................................ 132/90; 132/89
[58] Field of Search ............................ 132/90, 89, 91; 433/147, 146

[56] References Cited

U.S. PATENT DOCUMENTS

| 4,033,007 | 7/1977 | Hadary | 132/90 |
| 4,397,327 | 8/1983 | Hadary | 132/90 |
| 4,520,833 | 6/1985 | Hadary | 132/90 |

Primary Examiner—Gene Mancene
Assistant Examiner—John G. Weiss
Attorney, Agent, or Firm—Dennis H. Lambert

[57] ABSTRACT

A toothpick holder for holding a toothpick with a wedge-shaped cross-sectional configuration in different adjusted positions to facilitate access to different areas of the mouth, comprises an elongate handle with a shaped opening through one end thereof and a toothpick retainer having a stem received in the opening of the handle. The stem and opening have complementally shaped indexing portions which may be brought into and out of mating engagement to selectively detain the retainer in an adjusted position or permit its rotation in the opening to move it to a different adjusted position.

13 Claims, 16 Drawing Figures

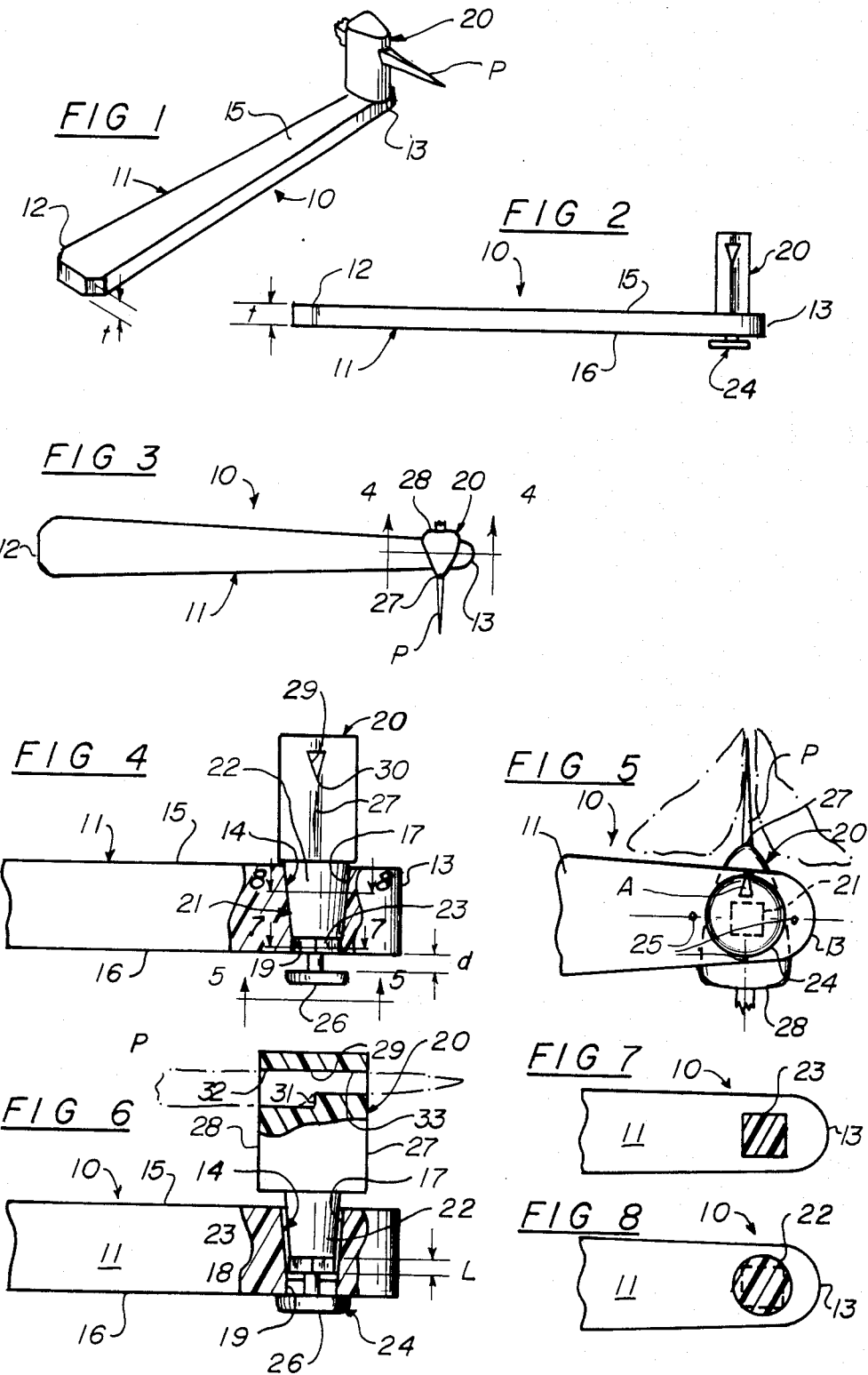

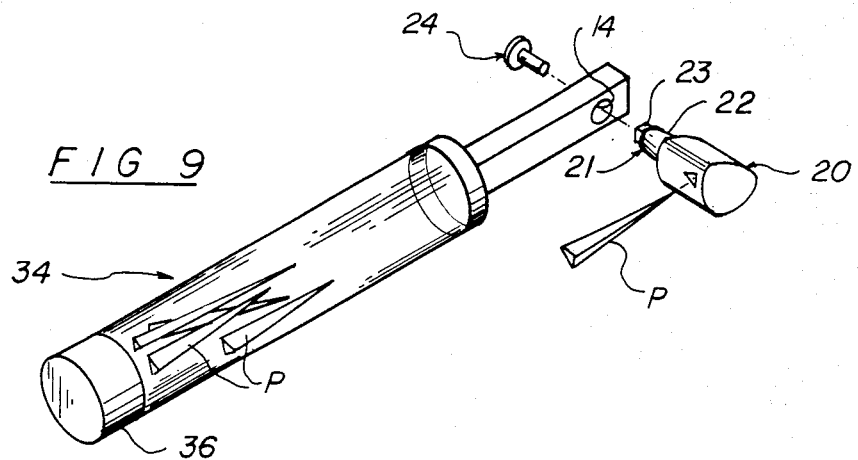
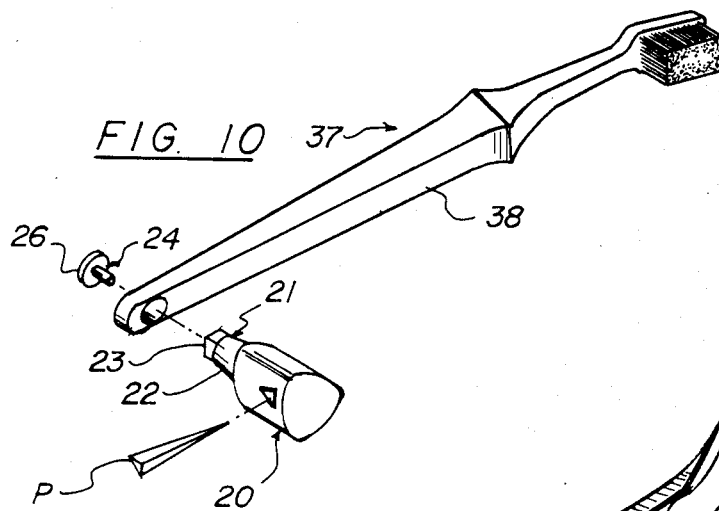
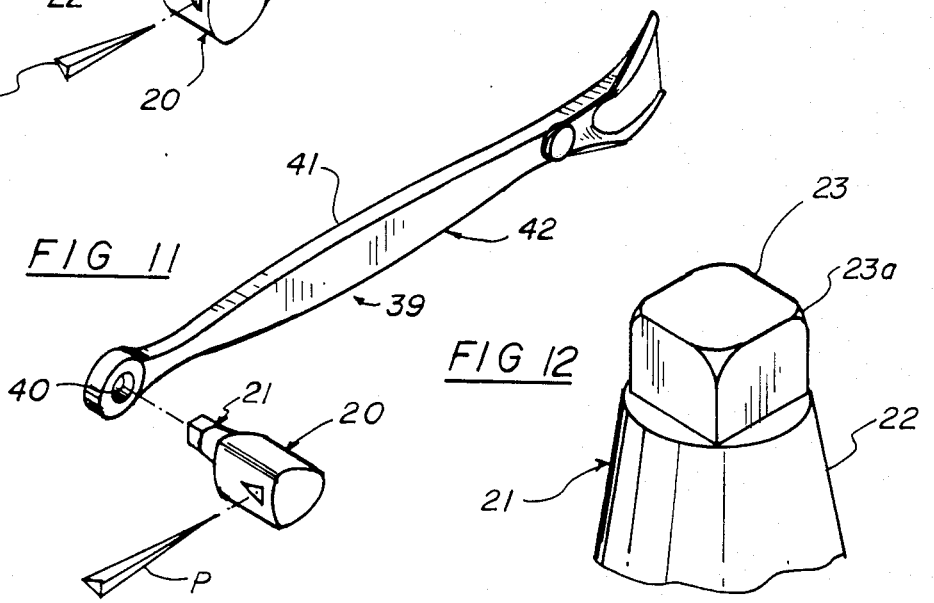
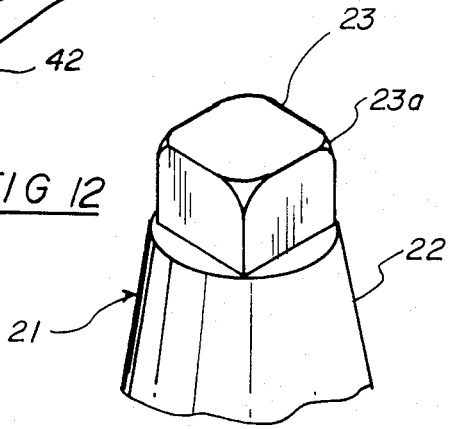

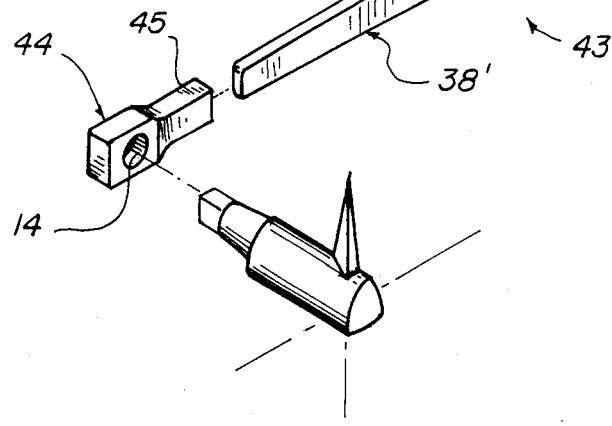
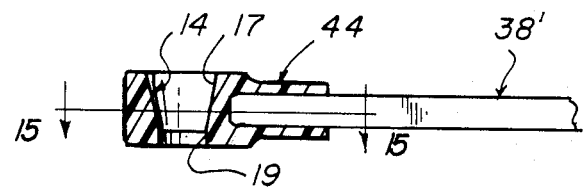
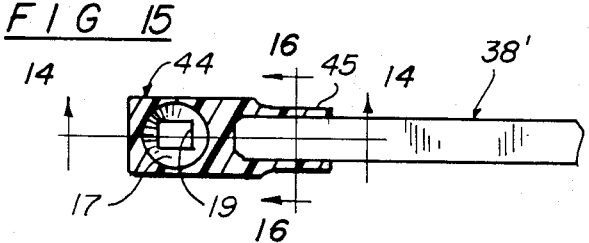
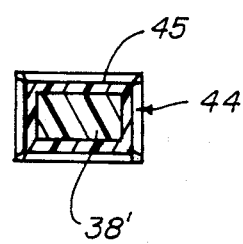

TOOTHPICK HOLDER

BACKGROUND OF THE INVENTION

1. Field of the Invention

This invention relates to dental implements, and more particularly, to a toothpick holder for positively holding a toothpick in any one of a plurality of selected orientations for facilitating access to different areas of the mouth.

2. Prior Art

Proper and frequent cleaning of the teeth is necessary for maintaining oral hygiene and healthy teeth and gums. While brushing is the most common method of cleaning teeth, it is not entirely satisfactory and the dental profession recommends other methods of cleaning as well, such as flossing. Moreover, the proper use of toothpicks is beneficial in any oral hygiene program, particularly for cleaning between the teeth.

Although flossing is the generally preferred method for removing plaque from the interdental or proximal spaces, there are many people who do not use floss because they simply cannot develop the skill it requires to floss. Others reject floss and its associated paraphernalia of special holders and threaders. In a search for acceptable alternatives to floss prompted by the existence of a significant number of non-flossers, several studies have been made of other types of interdental cleaners. These studies indicate that wedge-shaped toothpicks are superior to round toothpicks, and that wedge-shaped toothpicks can be as effective as floss provided they can contact the full width of the teeth bordering the interdental spaces. But when held by the fingers, which is the common manner of holding a toothpick, the toothpick can only contact the buccal, or front half of the teeth, while leaving the back half or lingual side of the teeth virtually untouched, thus allowing plaque to accumulate.

The plaque removing effectiveness of toothpicks can be increased with properly designed aids which enable the user to insert the toothpick into the back half of the interdental spaces and into contact with the lingual portion of the tooth sides. The PerioAid brand dental aid, or other dental aids with an arrangement for the insertion of a toothpick are examples of such aids. All of these aids, however, depend upon round toothpicks which are considerably less effective than wedge-shaped or triangular toothpicks and, of course, floss.

However, except for a few attempts at developing a toothpick holder, people are generally limited to the use of toothpicks held in the user's hand. Accordingly, the use of a toothpick is only partially effective in cleaning the teeth, and those areas which are difficult to reach are usually not cleaned. Additionally, roughly two-thirds of a full length toothpick serves as a handle for manipulating the pointed end in the spaces between the teeth. This means that two-thirds more raw material is required than is actually incorporated in the working (pointed) end. With this invention, however, shorter toothpicks can be used, resulting in a savings in raw material, packaging and shipping costs.

Examples of prior art toothpick holders are shown in U.S. Pat. Nos. 710,498, 1,291,282, 3,850,182, 3,892,040 and 4,397,327. In U.S. Pat. No. 710,498 a quill-like member is curved to form a pick. U.S. Pat. No. 1,291,282 discloses a threaded holer having a pair of openings therein for receiving a toothpick in either of two different positions. U.S. Pat. No. 3,850,182 discloses a floss holder for use on a toothbrush, wherein the holder is engaged on the end of the toothbrush handle via a socket-like connector. U.S. Pat. No. 3,892,040 discloses a holder having a threaded sleeve which is movable against a round toothpick to clamp the toothpick in position. U.S. Pat. No. 4,397,327 discloses a toothpick holder in which the toothpick is carried by a holder or retainer that may be positively latched in any one of a plurality of positions on a handle by means of a spring loaded latch.

None of the devices described in the above patents comprises a holder for holding a toothpick with a wedge-shaped cross-section in any one of a number of different orientations for properly orienting the wedge-shaped toothpick for access to different areas of the teeth at different sides of the mouth, and wherein the holder comprises a toothpick retainer frictionally secured on a handle.

SUMMARY OF THE INVENTION

It is, therefore, a primary object of this invention to provide a toothpick holder which is economical and simple in construction and which has a shaped socket for securely holding a toothpick in any of a plurality of selected orientations to facilitate access to different areas of the teeth.

Another object of the invention is to provide a toothpick holder which has a shaped opening at one end of a handle for holding a toothpick retainer in different predetermined orientations on the handle.

A more specific object of this invention is to provide a toothpick holder for holding a toothpick having a wedge-shaped cross-section, in which the toothpick may be inserted into a shaped opening in a toothpick retainer and the retainer frictionally held in any selected one of a plurality of different orientations on a handle for properly orienting the toothpick for one side of the mouth or the other, depending upon which orientation is given to the retainer and toothpick.

A further object is to provide a retainer for frictionally holding a toothpick, in which the retainer is shaped so as to present a narrow frontal area toward the teeth being treated, thus facilitating entry of the toothpick into the spaces between the teeth.

These and other objects and advantages of the invention are accomplished by a toothpick holder having an elongate handle with a shaped opening at one end, and a retainer with a shaped stem for frictional engagement in the opening to frictionally hold the retainer to the handle and positively hold the retainer in a selected position, to facilitate access to the spaces between the teeth at different sides of the mouth, and on both the front and rear surfaces of the teeth. Moreover, the retainer has a cross-sectional shape which presents a narrow profile or frontal area toward the teeth, thus facilitating entry of a toothpick carried thereby into the spaces between the teeth.

BRIEF DESCRIPTION OF THE DRAWINGS

These and other objects and advantages of the invention will become apparent from the following detailed description and accompanying drawings, wherein like reference characters designate like parts throughout the several views, and wherein:

FIG. 1 is a perspective view of a first and preferred form of the invention;

FIG. 2 is a side view in elevation of the form of the invention shown in FIG. 1;

FIG. 3 is a top plan view of the toothpick holder of FIGS. 1 and 2;

FIG. 4 is a greatly enlarged, fragmentary view shown partly in section and is taken along line 4—4 in FIG. 3;

FIG. 5 is an enlarged fragmentary view taken along line 5—5 in FIG. 4;

FIG. 6 is an enlarged view shown partly in section of the toothpick retainer of FIGS. 1 through 5;

FIG. 7 is a fragmentary sectional view taken along line 7—7 in FIG. 4;

FIG. 8 is a fragmentary sectional veiw taken along line 8—8 in FIG. 4;

FIG. 9 is an exploded perspective view of a second form of the invention;

FIG. 10 is an exploded perspective view of a third form of the invention;

FIG. 11 is an exploded perspective view of a fourth form of the invention;

FIG. 12 is an enlarged, fragmentary top perspective view of the indexing end of the stem of the retainer;

FIG. 13 is an exploded perspective view similar to FIG. 10 of a fifth form of the invention, wherein the retainer is attached to the handle of a toothbrush via an adapter;

FIG. 14 is an enlarged, fragmentary sectional view of the holder of FIG. 13, taken along line 14—14 in FIG. 15;

FIG. 15 is an enlarged fragmentary sectional view of the holder of FIG. 13 and is taken along line 15—15 in FIG. 14; and FIG. 16 is a transverse sectional view taken along line 16—16 in FIG. 15.

DESCRIPTION OF THE PREFERRED EMBODIMENTS

Referring more specifically to the drawings, a first form of the invention is indicated generally at 10 in FIGS. 1 through 8 and comprises an elongate handle 11 of substantially constant thickness "t" and tapering from a first end 12 which is approximately twice as wide as it is thick to a second end 13 which is approximately as wide as it is thick. The second end 13 has a shaped opening 14 extending therethrough from the top or front surface 15 thereof to the bottom or back surface 16. As seen best in FIGS. 4, 7 and 8, the shaped opening 14 has a frustoconically shaped entry portion 17 leading from the front surface 15 to an inner end 18 spaced closely adjacent the back surface 16, and an indexing portion 19 extending from the inner end 18 through the back surface 16. The indexing portion has a polygonal shape, preferably square or rectangular as shown.

A toothpick retainer 20 is secured to the handle 11 at the second end thereof by means of a shaped stem 21 received in the shaped opening 14. The stem comprises a frustoconically shaped portion 22 shaped complementally to the entry portion 17 of opening 14 in the handle 11, and a short indexing portion 23 shaped complementally to the indexing opening 19 and adapted to be moved into and out of registry with the opening 19. A retainer and actuator 24 extends from the end of the stem and projects beyond the back surface of the handle a distance "d" slightly greater than the length "L" of the indexing portion 23 when the stem is fully seated in the opening 14 as shown in FIG. 4. When the actuator 24 is pressed, the stem is moved forwardly to the position shown in FIG. 6, with the indexing portion 23 out of registry with the indexing opening 19, whereby the retainer 20 may be rotated about its axis to different adjusted positions. When the retainer has been rotated to a desired position, marked by arrow "A" and indexing marks 25, it is again pressed inwardly to place the indexing portion 23 in the indexing opening 19 and secure the retainer in the adjusted position. As seen in FIGS. 4 and 6, the actuator 24 has an enlarged head 26 which overlies the opening 19 and prevents withdrawal of the stem out of the opening 14 any more than is necessary to remove the indexing portion 23 from indexing opening 19. The actuator may be integrally molded with the stem or formed separately and attached thereto by adhesive, a press fit or the like.

The retainer 20 is slightly elongate with a triangular or arrow-head shaped transverse cross-section, presenting a narrow leading edge 27 and a broader rearward surface 28. A shaped opening 29 extends from the rear surface 28 through the leading edge 27 and has a shaped configuratioin as more fully described in applicant's prior U.S. Pat. No. 4,520,833. Basically, the shaped opening 29 is wedge-shaped in transverse cross-section, with the apex 30 thereof pointing toward the stem end or handle of the retainer and having a stepped diameter defining a shoulder 31 between the entry and exit ends 32 and 33, respectively, of the opening 29. Consequently, when a toothpick "P" is inserted into the opening from the entry end 32 thereof it engages the shoulder and is firmly wedged in the opening. As shown in the drawings, the toothpick is of the triangular or wedge-shaped cross-sectional variety and is typically made of wood. The narrow leading edge 27 of the retainer enables the retainer to be moved into closer proximity with the teeth, as shown in FIG. 5, whereby the toothpick "P" may be more efficiently inserted into the space between the teeth without interference between the retainer and teeth.

A first modification of the invention is shown at 34 in FIG. 9 and includes a retainer 20 identical to that shown and described in FIGS. 1 through 8. However, rather than the handle 11 as in the first form of the invention, this form comprises a storage handle 35 having a removable cap 36 and adapted to store spare toothpicks "P" or like objects, if desired.

A second modification of the invention is shown at 37 in FIG. 10 and in this form of the invention the retainer 20 is inserted in a shaped opening 14 formed in the end of the handle 38 of a conventional toothbrush, such as that sold under the trademark "Reach" by Johnson & Johnson.

A third modification of the invention is shown at 39 in FIG. 11 and in this form of the invention the retainer is inserted in a shaped opening 40 in the end of the handle 41 of a floss holder 42 such as that illustrated and described in U.S. Pat. No. 4,041,962. In other words, the bushing 1e and pick 2 are replaced with the retainer 20 and pick "P" of the invention. Moreover, in this form of the invention, the "mushroom-shaped" actuator 24 is omitted and the indexing portion 23 is made longer so that when the stem 21 is fully seated in the opening 14 it projects from the rear surface of the handle, enabling it to be pushed to release the indexing portions and permit turning of the toothpick retainer to a different position.

As seen best in FIG. 12, the extreme end portion of corners 23a of the indexing end 23 of the stem 21 is slightly rounded, permitting turning of the retainer in the opening 14 prior to full insertion of the stem in the opening and facilitating adjustment of the retainer on the handle. In other words, the rounded corners cause the end of the stem to act as a pilot, guiding the indexing portion into the indexing opening.

A fourth modification of the invention is shown at 43 in FIGS. 13 through 16. In this form of the invention, an adapter sleeve 44 has a sprocket-shaped end 45 into which the end of the toothbrush handle 38' may be inserted. The socket 45 has sufficient elasticity to enable the toothbrush handle to be inserted into the adapter and yet snugly retain the adapter in place on the handle. This structure enables the toothpick holder to be used with any toothbrush and does not require any specific opening through the handle. The other end of the adapter has a shaped opening 14 therethrough, comprising a frustoconically shaped portion 17 and an indexing portion 19 just as in the previously described forms of the invention.

The toothpicks may comprise "Stim-U-Dent" brand toothpicks as manufactured by Johnson & Johnson, or other suitable, shaped toothpicks. In use, the toothpicks are fully inserted into the opening of the retainer and the unused portion projecting rearwardly of the retainer is broken off. Alternatively, specially manufactured shorter toothpicks may be used to avoid wasting the excess material broken off with conventional toothpicks.

While the invention has been shown and described in detail herein, it is to be understood that various changes in construction may be made without departing from the scope of the invention as defined in the claims appended hereto.

Having thus described the invention, what is desired to be secured by Letters Patent is:

1. A toothpick holder for holding a toothpick in different adjusted positions to facilitate access to different portions of the mouth, comprising:
   an elongate handle having a shaped opening in one end thereof, said shaped opening having an entry portion and a polygonally shaped indexing portion formed therein; and
   a toothpick retainer having a stem inserted into the shaped opening of the handle to hold the retainer to the handle in different adjusted positions, said stem having a portion shaped complementally to the entry portion of the opening in the handle and an indexing portion shaped complementally to the indexing portion of the opening in the handle, said stem being movable axially in the opening to selectively place the indexing portion thereof into and out of the indexing portion of the opening, whereby when the indexing portions of the stem and opening are in mating engagement the stem is secured against rotational movement in the opening and when they are out of engagement the stem may be rotated in the opening to move the retainer to a different adjusted position.

2. A toothpick holder as claimed in claim 1, wherein:
a retainer actuator projects from one end of the stem through the indexing opening and has an enlarged end overlying the indexing opening, the spacing between the enlarged end and the end of the stem being slightly greater than the length of the indexing portion of the opening, whereby the stem may be pressed into the opening to bring the indexing portion thereof into mating engagement with the indexing portion of the opening to secure the retainer in an adjusted position on the handle, and the actuator may be pressed to move the indexing portions of the stem and opening out of mating engagement whereby the stem may be rotated about its axis in the opening to move the retainer to a different adjusted position on the handle, the enlarged end serving as a stop to prevent withdrawal of the stem from the opening.

3. A toothpick holder as claimed in claim 1, wherein:
indexing marks are on the retainer and handle to visually indicate the adjusted positions of the retainer on the handle.

4. A toothpick holder as claimed in claim 1, wherein:
the retainer has a generally triangularly shaped transverse cross-sectional configuration, defining a narrow leading edge and a broader rear surface, and a toothpick-receiving opening extending from the rear surface through the leading edge to receive a toothpick with the pointed end of the toothpick projecting from the narrow leading edge of the retainer, whereby the retainer may be positioned closely adjacent the teeth to facilitate entry of the toothpick into the space between the teeth without interference between the retainer and the teeth.

5. A toothpick holder as claimed in claim 2, wherein:
the retainer has a generally triangularly shaped transverse cross-sectional configuration, defining a narrow leading edge and a broader rear surface, and a toothpick-receiving opening extending from the rear surface through the leading edge to receive a toothpick with the pointed end of the toothpick projecting from the narrow leading edge of the retainer, whereby the retainer may be positioned closely adjacent the teeth to facilitate entry of the toothpick into the space between the teeth without interference between the retainer and the teeth.

6. A toothpick holder as claimed in claim 5, wherein:
indexing marks are on the retainer and handle to visually indicate the adjusted positions of the retainer on the handle.

7. A toothpick holder as claimed in claim 6, wherein:
the toothpick-receiving opening through the retainer has a triangularly shaped transverse cross-sectional configuration for receiving and holding toothpicks having a like transverse cross-section.

8. A toothpick holder as claimed in claim 1, wherein:
the handle comprises a hollow, tubular storage handle for receiving and holding a number of toothpicks for use in the holder.

9. A toothpick holder as claimed in claim 1, wherein:
the handle comprises the handle of a toothbrush.

10. A toothpick holder as claimed in claim 1, wherein:
the handle comprises the handle of a floss holder.

11. A toothpick holder as claimed in claim 1, wherein:
the entry portion of the shaped opening is circular in transverse cross-section, and the indexing portion of the shaped opening is polygonal in transverse cross-section; and
the indexing portion of the stem has a rounded end edge portion to facilitate entry of the stem indexing portion into the indexing opening and enables turning of the stem in the opening prior to full insertion of the stem into the opening.

12. A toothpick holder for holding a toothpick in different adjusted positions to facilitate access to different portions of the mouth, comprising:
an elongate toothbrush handle having first and second ends and having bristles at one end thereof;

an adapter sleeve received over the other end of the toothbrush handle, said adapter sleeve having a shaped opening formed therein, said shaped opening having an entry portion and a polygonally shaped indexing portion; and a toothpick retainer having a stem inserted into the shaped opening to hold the retainer to the adapter sleeve and thus to the handle in different adjusted positions, said stem having a portion shaped complementally to the entry portion of the opening in the adapter sleeve and an indexing portion shaped complementally to the indexing portion of the opening, said stem being movable axially in the opening to selectively place the indexing portion thereof into and out of the indexing portion of the opening, whereby when the indexing portions of the stem and opening are in mating engagement the stem is secured against rotational movement in the opening and when they are out of engagement the stem may be rotated in the opening to move the retainer to a different adjusted position.

13. A toothpick holder as claimed in claim 12, wherein:

the shaped opening is formed through the adapter along an axis perpendicular to the axis of the toothbrush handle.

* * * * *